United States Patent [19]

Beers

[11] Patent Number: 5,083,036

[45] Date of Patent: Jan. 21, 1992

[54] INDICATOR CIRCUIT FOR A CONCENTRATION MEASURING APPARATUS

[75] Inventor: Howard L. Beers, North Fort Myers, Fla.

[73] Assignee: HF Scientific, Inc., Fort Myers, Fla.

[21] Appl. No.: 641,180

[22] Filed: Jan. 15, 1991

[51] Int. Cl.⁵ .............................................. G01N 21/00
[52] U.S. Cl. ..................................... 250/565; 356/224
[58] Field of Search ................ 250/565, 564; 356/224, 356/218, 219

[56] References Cited

U.S. PATENT DOCUMENTS

| | | | |
|---|---|---|---|
| 3,973,852 | 8/1976 | Moore et al. | 250/564 |
| 4,095,117 | 6/1978 | Nagy | 250/564 |
| 4,908,676 | 3/1990 | Bedell et al. | 250/565 |

Primary Examiner—David C. Nelms
Assistant Examiner—T. Davenport
Attorney, Agent, or Firm—William E. Noonan

[57] ABSTRACT

An indicator circuit is provided for an apparatus that measures the concentration of a selected component in a test sample. The apparatus generates a test voltage that represents the concentration of the component in the test sample. The circuit generates a series of range voltages, each of which represents a respective one of a series of potential concentration ranges of the component in the test sample. A switching circuit selects an adjacent pair of range voltages immediately above and below the test voltage and applies the selected range voltages across an incremental voltage divider such that the voltage difference of the selected range voltages is divided into a series of incremental voltages, each of which represents a respective one of a series of potential incremental concentration levels of the component within each concentration range. The test voltages are compared with each of the incremental concentration voltages and the actual incremental concentration level of the component in the test sample is determined. There is a group of incremental indicator elements, each of which represents and displays a respective incremental concentration level in each of the concentration ranges.

17 Claims, 2 Drawing Sheets

INDICATOR CIRCUIT FOR A CONCENTRATION MEASURING APPARATUS

FIELD OF THE INVENTION

This invention relates to an indicator circuit for an apparatus that measures the concentration of a selected component in a test sample, and more particularly, to an indicator circuit for a photometer.

BACKGROUND OF THE INVENTION

Photometers are widely employed for measuring the concentration of selected components or ingredients in a sample medium. For example, such instruments may be employed to test for the concentration of chlorine or other constituent chemicals in drinking or pool water. Typically, a photometer detects light transmitted through a sample medium and provides a voltage signal that is indicative of the intensity of that light. This value is logarithmically related to the concentration of the component being measured. A number of known devices employ analog instrumentation to calculate the concentration, which is typically displayed, in terms of absorption, by a vernier scale or similar means. Such a display is often difficult to read and interpolate, particularly at higher concentration levels where the scale is severely compressed due to its logrithmic nature. Moreover, because the test results are displayed in terms of absorption, the user must resort to reference tables in order to determine the concentration. This complicates the testing procedure considerably and particularly hinders field testing.

Alternatively, digital microprocessors may be employed to compute the concentration. However, such devices require software which must be programmed into the microprocessor thereby adding to the complexity and expense of the device.

Various indicator circuits employ LED's or Nixie tubes to display a measured voltage or concentration level. However, none of these circuits provides a simple and satisfactory means for instantaneously and accurately indicating incremental levels of concentration between broad concentration ranges; for example, where the broad range of concentration is measured in parts per million and, incremental measurements on the order of tenths of parts per million are required. Conventional indicator circuits, such as the circuit shown in U.S. Pat. No. 3,703,002, employ LED or Nixie tube indicators wherein a respective light is assigned to each incremental level. Thus, if a concentration range of 0-4 ppm is being tested and an accuracy of 0.1 ppm is required, 40 individual indicators must be employed. Such a display is inordinately large and difficult to decipher. It requires a photometer that is much too large for use in the field. Moreover, such an array of indicators is wholly impractical where a very high degree of accuracy is required.

Performing rapid and reliable null or zeroing calibrations is a further problem encountered by conventional photometers. Such calibrations are typically required to compensate for spurious readings caused by components in the sample medium other than the component being measured. Conventional means for accomplishing zeroing calibrations include manual adjustments and microprocessors. Manual adjustments are time consuming and subject to human error. Microprocessor calibration requires the complexity and expense of software. Although certain automatic zeroing circuits are known, these are typically utilized in "two cuvette" photometers wherein separate beams of light are transmitted through respective cuvettes containing a reference medium and a test medium. To date, no system is known for providing automatic and accurate zeroing calibration in a single cuvette photometer.

SUMMARY OF THE INVENTION

It is therefore an object of this invention to provide an indicator circuit that accurately and rapidly determines and displays the concentration of a selected component in a sample medium.

It is a further object of this invention to provide an indicator circuit that employs a simplified, compact and yet highly accurate display for indicating measured incremental concentration levels.

It is a further object of this invention to provide an indicator circuit that measures and displays concentration directly without the inconvenience and unreliability associated with analog scale displays and without the expense and programming requirements of conventional digital displays.

It is a further object of this invention to provide an indicator circuit that is particularly advantageous for use in a compact, hand held photometer.

It is a further object of this invention to provide a single cuvette photometer that provides for quick, accurate and automatic zeroing calibration of a sample medium.

It is a further object of this invention to provide a photometer that is particularly useful for field testing the concentration of a variety of substances.

This invention results from a realization that, in a photometer, the relationship between the voltage difference representing a particular incremental concentration level in a broad range of concentrations and the voltage drop across the range is constant for the corresponding incremental level in any and all other broad concentration ranges of like magnitude. As a result, an indicator circuit can be constructed employing a single set of incremental concentration level indicator elements that operate in a number of discrete concentration ranges.

This invention results from a further realization that even where a non-linear (e.g. logarithmic) relationship exists between concentration and voltage, direct measurements of concentration can be made without resorting to tables, scales, analog interpretation or software by developing, through properly constructed voltage dividers, a plurality of standard or reference voltages that correspond to predetermined levels of concentration.

As used herein, "concentration ranges" refer to discrete, relatively broad bands of continuous concentration levels. For example, the concentration ranges may be defined by whole number units of parts per million (ppm). In such an embodiment, the range "0 ppm" refers to concentration levels of 0-0.9 ppm; the range "1 ppm" refers to 1 ppm -1.9 ppm; and so on. "Incremental concentration levels" refer to the discrete increments within each concentration range. The preferred incremental levels described herein are tenths of parts per million (0.1 ppm increments). It should be understood, however, that the invention may be practiced with various other concentration ranges and incremental levels.

This invention features an indicator circuit in an apparatus for measuring the concentration of a selected component in a test sample, which apparatus includes means for generating a test voltage that represents the concentration of the component in the test sample. The indicator circuit comprises means for generating a series of range voltages, each of which represents a respective one of a series of potential concentration ranges of the component in the test sample. There are incremental voltage divider means and switching means for selecting an adjacent pair of range voltages, one of which is below and the other of which is at least as great as the test voltage. The selected range voltages are applied across the incremental voltage divider means. As a result, the voltage difference of the selected range voltages is divided into a series of incremental voltages, each of which represents a respective one of a series of potential incremental concentration levels of the component within each concentration range. There are incremental computation means for comparing the test voltage with each of the incremental concentration voltages and determining the actual incremental concentration level of the component in the test sample. There are also a group of incremental indicator elements, each of which represents a respective incremental concentration level in each of the concentration ranges. The incremental indicator elements are responsive to the incremental computation means for indicating the determined incremental concentration level of the component in the test sample.

In a preferred embodiment, the incremental computation means may include a group of incremental level comparators, each of which compares the test voltage with a respective incremental concentration voltage to provide an output representing the strength of the test voltage relative to that of the respective incremental concentration voltage. The incremental computation means may further include incremental logic means, responsive to the outputs of the incremental comparators, for directing the incremental indicator elements to indicate the incremental concentration level of the component in the test sample.

Range computation means, responsive to the means for generating a test voltage, may be employed for comparing the test voltage with each of range voltages and determining the actual concentration range of the components in the test sample. Range indicator means, responsive to the range computation means, may be used for indicating the determined concentration range of the component. The range computation means may include a group of range comparators, each of which compares the test voltage with a respective range voltage to provide an output representing the strength of the test voltage relative to that of the respective range voltage. The range computation means may further include range logic means, responsive to the outputs of the range comparators, for directing the range indicator means to indicate the concentration range of the component in the test sample. The range indicator means may include a group of range indicator elements, each of which represents a respective concentration range.

Means may be provided for generating a reference voltage that represents a known concentration of the component in the reference sample, as well as the test voltage. A range voltage divider may be employed for dividing the reference voltage into the plurality of range voltages, each of which is a function of the reference voltage. Each range voltage may be linearly or non-linearly related to the reference voltage. In a preferred embodiment described herein the range voltage is logarithmically related to the reference voltage.

This invention also features a single cell photometer for measuring the concentration of a selected component in a sample medium. The photometer includes a selectively actuatable light source and means for alternately holding, in the optical path of the light source, one of a reference sample that represents a known concentration of the component in the medium and a test sample that represents the concentration to be measured. There are detector means for sensing the intensity of light transmitted through the reference sample and the test sample in a selected wavelength region. Such detector means generate an output voltage representative of the sensed intensity. There are first means for actuating the light source to transmit light through the reference sample. Means, responsive to the first means for actuating, generate and store a reference voltage that corresponds to the intensity sensed by the detector means when light is transmitted through the reference sample. There are second means for actuating the light source to transmit light through the test sample such that the output voltage comprises a test voltage. The photometer also includes an indicator circuit as summarized above.

Preferably, the means for generating a reference voltage includes means for developing a staircase voltage that increases until it corresponds to the output voltage representing the intensity of light transmitted through the reference sample. The means for developing may include a pulse counter having an input and an output, a resistor ladder connected to the output of the counter and means, connected to the input of the counter, for driving the counter to provide a pulsed output signal to the resistor ladder such that the ladder transforms the pulsed signal into the staircase voltage. The means for driving may include an oscillator. The means for generating may include means for comparing the staircase voltage and the output voltage and latching the means for developing in a condition that maintains the staircase voltage at a level that corresponds to the output voltage. The means for actuating may include test timer means for holding the light source on for a predetermined time to transmit light through the test sample.

DETAILED DESCRIPTION OF PREFERRED EMBODIMENT

Other objects, features and advantages will result from the following description of preferred embodiments and the accompanying drawings, in which FIG. 1 is an elevational front view of a photometer that includes the indicator circuit of this invention.

Figure 1:
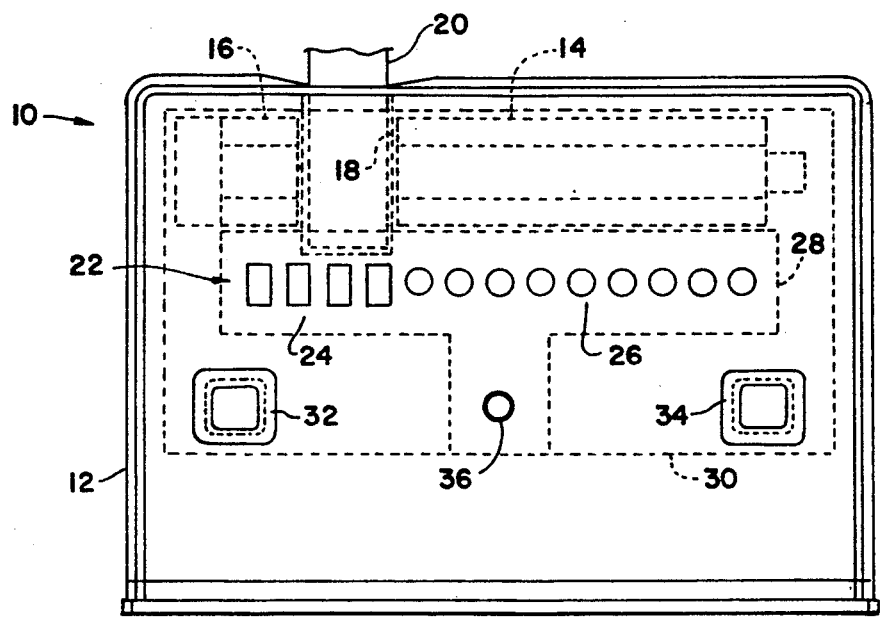

An indicator circuit according to this invention measures and displays the concentration of a selected chemical component in a liquid or gas test sample. The circuit is particularly advantageous for use in a single cell photometer or other instruments that are used to measure concentration. The circuit employs a reference voltage that is divided into a plurality of range voltages. The reference voltage represents a known, i.e. 0% concentration level of the component being tested. Each range voltage is a function of the reference voltage and represents one of a continuous series of potential concentration ranges.

The reference voltage may be generated by various means. Preferred means include an automatic zeroing circuit that is disclosed by this invention. A cuvette or other container is filled with the sample medium to be tested and light is transmitted through that medium and detected in a selected wavelength band by a photosensor to provide an initial voltage that represents a zero concentration. The automatic zeroing circuit develops a voltage which equals this zero concentration voltage and stores that voltage as a reference voltage for subsequent comparison against the measured test voltage. The test voltage is developed by adding a predetermined reagent to the sample medium and again transmitting light through the sample for detection by the photosensor. Such reagents are conventionally known and used in the photometric art.

The zeroing circuit negates the effect that components of the sample medium other than the selected component may have on the sensed intensity. The absorption characteristics of components other than chlorine should remain consistent in the reference and test samples, and as a result, the effects of those components are negated so that the instrument is calibrated.

The range voltages are typically developed from the reference voltage by use of a range voltage divider that includes resistors having values that are selected to provide voltages that correspond to the selected concentration values at the lower end of each range. The measured test voltage is then compared against each of these concentration values and logic is employed to determine the actual concentration range of the component being tested. The detected concentration range is then directly displayed, preferably by a first group of indicator elements.

The range voltages employed for testing chlorine in water are determined in the following manner. It is known that the percentage of light absorbed by the chlorine in the water is directly related to the concentration of chlorine as follows:

| FRACTION OF LIGHT ABSORBED | CONCENTRATION |
|---|---|
| 1.00 | 4 parts per million (ppm) |
| .75 | 3 ppm |
| .50 | 2 ppm |
| .25 | 1 ppm |
| 0 | 0 ppm |

At chlorine levels above 4 ppm, effectively all of the light is absorbed. However, for most testing purposes this limitation is acceptable. It is further known that absorption is related to the transmission of light through the sample in the following manner:

$$A = \log\left(\frac{1}{T}\right)$$

The light transmission T is directly related to a particular voltage level; the larger the voltage, the larger the greater the intensity T. Accordingly, the relative voltage is logarithmically related to the absorption and concentration levels and the voltage divider can be constructed so that the selected range voltages correspond to the desired ranges of concentration, i.e. 1 ppm, 2 ppm, 3 ppm and 4 ppm. The relative voltage that indicates 0 ppm (i.e. 0 absorption) is derived as follows:

$$A = \log\left(\frac{1}{T}\right),$$

$$\log^{-1}(0) = \frac{1}{T},$$

$$T = \frac{1}{\log^{-1}(0)} = \frac{1}{1} = 1$$

Therefore, a relative voltage level of 1 VR, or 100% of VR, represents 0 ppm. Relative voltage levels that are less than VR indicate that light is being absorbed and the concentration of chlorine is greater than 0 ppm.

The appropriate relative voltage level that corresponds to 2 ppm (i.e. absorption =0.5) is derived as follows:

$$A = \log\left(\frac{1}{T}\right),$$

$$.5 = \log\left(\frac{1}{T}\right),$$

$$\log^{-1}(.5) = \frac{1}{T},$$

$$3.163 = \frac{1}{T},$$

$$T = .316$$

Accordingly, a range voltage of 0.316 VR corresponds to a concentration level of 2 ppm.

The voltages that correspond to 1 ppm, 3 ppm and 4 ppm are determined in an analogous manner. As a result, the relative range voltages are as follows:

| CONCENTRATION | VOLTAGE |
|---|---|
| 0 ppm | 1.0 VR |
| 1 ppm | .5623 VR |
| 2 ppm | .3162 VR |
| 3 ppm | .1778 VR |
| 4 ppm | .1000 VR |

A significant advantage of the range detecting portion of the indicator circuit is that it provides a direct reading of concentration regardless of whether the sensed voltage is a linear or non-linear function of the concentration. Interpolation, reference tables and software are not required. This system may be employed to provide direct and accurate indications of concentration range, where various other non-linear or linear relationships exist between the voltage and the concentration level.

The indicator circuit of this invention further comprises means for computing and displaying incremental concentration levels within each of the concentration ranges. Switching circuitry is employed for selecting the range voltages immediately above and below the test voltage. The selected range voltages are applied across an incremental voltage divider such that the voltage difference of the selected range voltages is divided into a series of incremental voltages. Each of the incremental voltages represents a respective one of a series of potential incremental concentration levels within each concentration range. The test voltages are compared with each of the incremental voltages and the actual incremental concentration level of the component is determined. A single group of incremental indicator elements is employed. Each element represents a respective incremental concentration level within each of the concentration ranges. In accordance with this invention, it has been determined that the ratio between a particular incremental voltage drop within a range and the voltage drop across that range is constant for each of the ranges being measured. Accordingly, a single set of incremental level indicator elements may be employed for all of the ranges and a much simpler and convenient display is provided.

In the embodiments disclosed herein, the incremental concentration levels are tenths of ppm. However, in alternative embodiments, various other incremental levels may be utilized.

There is shown in FIG. 1 a single cell photometer 10 for measuring the concentration of a selected component in a sample medium. Typically, the sample medium is a liquid, although the apparatus may be used for testing gases. The testing apparatus may be employed to measure the concentration of any varieties of components that are susceptible to photometric testing. A particularly preferred application of this apparatus is for testing the concentration of chlorine in drinking and pool water.

Apparatus 10 includes a housing 12 that is relatively compact and lightweight so that it may be transported conveniently in the field. Housing 12 accommodates an elongate light source 14 and a conventional photometric photocell detector unit 16 that are arranged on opposite sides of a test receptacle 18. The receptacle holds a cuvette 20, which accommodates the sample medium to be tested.

Photometer 10 further includes a plurality of indicator elements 22 that are arranged generally linearly across the front face of housing 12. In alternative embodiments, various other arrangements of indicator elements may be utilized. Elements 22 include a first group 24 of rectangular range indicator elements and a second group 26 of circular incremental level indicators. Each of the indicators 22 comprises a conventional LED or similar display means. Different respective shapes are employed for the range and incremental level indicators so that quick and unambiguous readings may be taken. Each of the indicator elements 22 is operably mounted within housing 12 on a PC board 30 and extends through a protective window 28 and the front face of housing 12. The indicator elements are activated in the manner described below to provide an indication of the concentration of a selected component in the sample medium carried by cuvette 20.

A second PC board mounted in housing 12 below board 30 carries an indicator circuit, which is described more fully in connection with FIG. 2. A pair of momentary push button actuator switches 32 and 34 are interconnected to the circuttry on the PC board and extend outwardly through the forward face of housing 12. Each of the switches 32 and 34 is resiliently biased outwardly from the housing and comprises a push button that is composed of rubber or similar material that facilitates operator engagement. Switch 32 serves as a "on" switch and further serves to provide zeroing calibration of the photometer. Actuator switch 34 is engaged so that the photometer reads a test sample and calculates and displays the actual concentration of the selected component in that sample. A lamp 32 is mounted on PC board 28 generally between switches 32 and 34. Lamp 36, which typically comprises an LED, is activated when switch 32 is engaged and thereby indicates that the photometer 10 has been turned on and that a zeroing calibration has been achieved. The functioning of switches 32 and 34 and lamp 36 are described in greater detail below.

Figure 2:
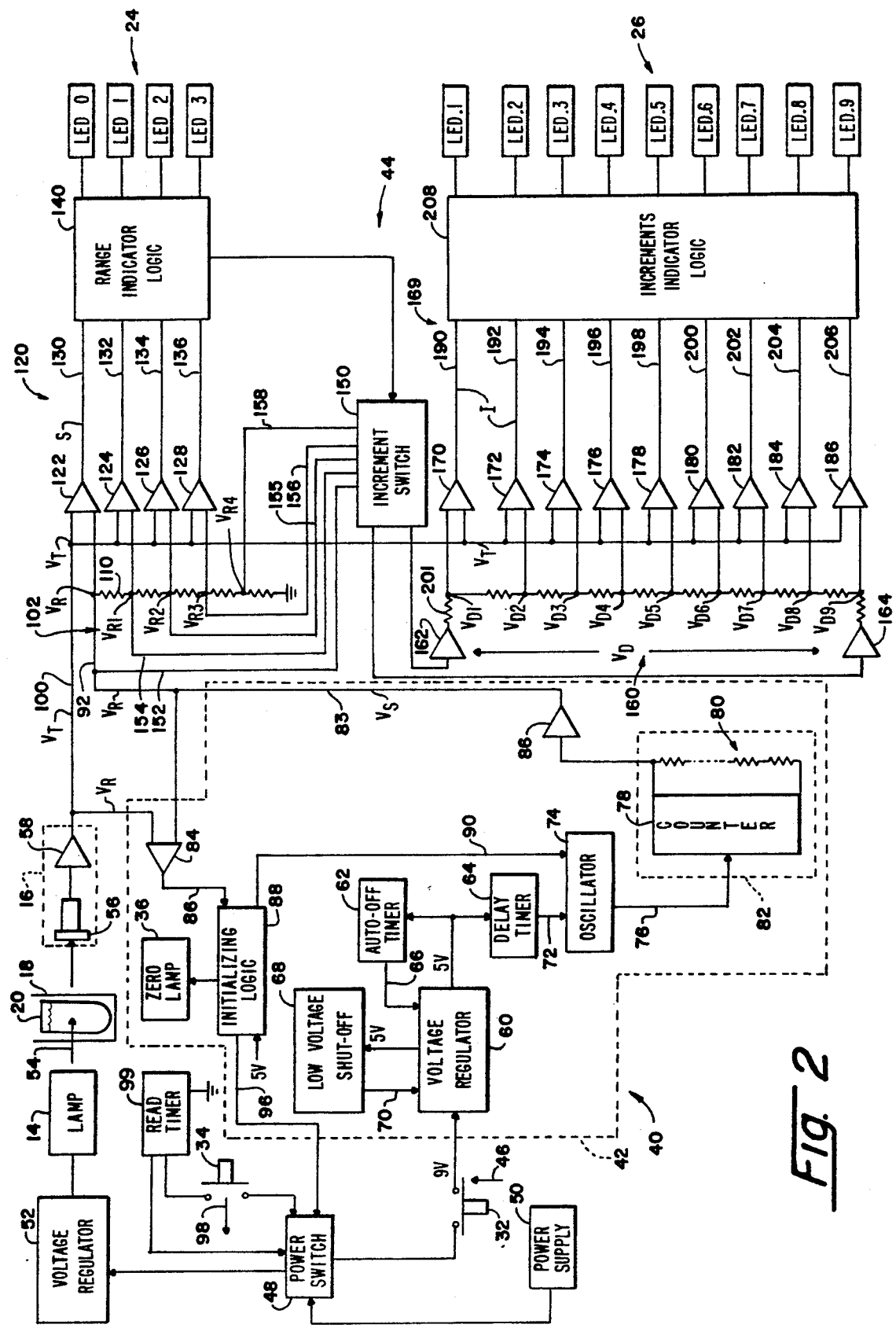
FIG. 2 is a schematic view of the indicator circuit of this invention.

Photometer circuitry 40, FIG. 2, includes an automatic zeroing circuit 42 for achieving a zero calibration and an indicator circuit 44 for determining and displaying the concentration of the selected component in the sample contained in cuvette 20. Initially, a cuvette containing a sample without reagent is placed in receptacle 18. This is known as the reference sample. When actuator switch 32 is closed in the direction of arrow 46, the photometer is activated. More particularly, a power switch 48 connects a power supply 50 to lamp 14 so that lamp 14 is energized. Power supply 50 typically comprises a 9 volt battery, although alternative power supplies may be employed. The voltage from the power supply to the lamp is regulated at 2.5 volts by voltage regulator 52. As a result, lamp 14 emits a broad band of radiation 54 that is transmitted through the sample medium contained in cuvette 20. The transmitted radiation is sensed by detector 16, which includes an interference filter 56 that limits the light transmitted to a selected wavelength region. Preferably this region is centered about 515 nanometers, plus or minus 10 nanometers, although in alternative embodiments various other wavelength bands may be selected. Detector 16 also includes an amplifier 58 that generates an output signal that is indicative of the intensity of the light transmitted through the cuvette. When the reference sample is contained in cuvette 20 light 54 transmitted through the sample causes detector 16 to generate a reference voltage VR.

When actuator button 32 is closed, power supply 50 also energizes zeroing circuit 42, which calibrates the photometer. More particularly, a 9 volt input is provided to voltage regulator 60, which provides a 5 volt output signal. This signal activates an automatic off timer 62 and a delay timer 64. Timer 62 commences timing and at the end of a predetermined time, (e.g. 8 minutes) provides a signal over line 66 to regulator 60, which deactivates the voltage regulator and turns off the photometer. This prevents excessive draining of power supply 50, which may occur if the photometer is unintentionally left in an "on" condition. Voltage regulator 60 also provides a 5 volt signal to a low voltage shut off circuit 68. This circuit senses the voltage level of power supply 50. If that level is too low, lamp 14 provides erratic radiation emissions which may cause inaccurate measurements. Accordingly, if the voltage level of power supply 50 is below a predetermined level, circuit 68 generates a signal over line 70 that turns off voltage regulator 60 to deactivate the instrument.

Delay timer 64 responds to the 5 volt signal from regulator 60 by timing out for a predetermined period (e.g. 0.5 seconds). After this period, it generates a signal over line 72 to an oscillator 74. Activation of the oscillator is delayed by timer 64 so that lamp 14 is provided with an opportunity to stabilize. Otherwise, if the oscillator is activated immediately, the lamp may produce unstable light emissions that can result in inaccurate readings. When activated, the oscillator provides a signal over line 76 that drives a binary counter 78. Counter 78 commences counting and produces a pulsed output voltage that is applied across an R/2R resistor ladder 80. Counter 78 and resistor ladde 80 may comprise a conventional D/A converter 82. As counter 78 continues counting, ladder 80 produces an ascending staircase voltage VS that is applied over line 83 as a first input to a comparator 84. A buffer amplifier 86 isolates ladder 80 from comparator 84.

The other input provided to comparator 84 is the reference voltage VR, which represents the intensity of light transmitted through the reference sample in cuvette 20. When the ascending staircase voltage VS reaches the level of reference voltage VR, comparator 84 provides a signal over line 86 to initializing logic 88. In response to this signal, logic 88 provides a signal over line 90 that deactivates oscillator 74. As a result, counter 78 is latched at a count that provides a staircase voltage VS that is equal to VR. This reference voltage VR is then provided over line 92 to the indicator circuit 44, where it is employed as described more fully below.

Initializing logic 88 further responds to the staircase voltage reaching VR by providing a signal which activates zero lamp 36 to indicate that the photometer has been zero calibrated. At the same time, the initializing logic 88 provides a signal over line 96 that instructs power switch 48 to deactivate lamp 14.

At the completion of this step, the zeroing circuit 40 provides a reference voltage VR that represents a transmission of 100% of the light through the sample medium, and thus a 0% concentration of the selected component in the sample medium. Cuvette 20 is then removed from receptacle 18 and a conventional photometric reagent is added to the sample. This reagent typically causes the sample to acquire a hue, which results from reaction of the reagent with the selected component that is being measured. The resulting hue indicates the degree of concentration of the selected component in the medium. A fainter hue indicates a lower concentration and a darker hue indicates a greater concentration.

After the reagent is added to cuvette 20, it is mixed well in the medium and the cuvette is replaced in receptacle 18. The sample medium containing reagent comprises the sample to be tested. Actuator switch 34 is closed in the direction of arrow 98 so that power switch 48 reconnects power supply 50 with lamp 14. As a result, the lamp is reactivated to transmit light 54 through the test sample in cuvette 20. Lamp 14 remains "on" for as long as switch 34 is held closed. If the switch is immediately released a read timer 99 holds the lamp on for a predetermined minimum time (e.g. 5 seconds). Photodetector 16 provides over line 100 a test voltage VT that represents the intensity of light transmitted through the test sample, and, therefore, the concentration of the selected component in the test sample.

Range computation means are utilized for determining the concentration range of the test sample. This includes a range voltage divider 102 comprising a resistor ladder that divides reference voltage VR into a plurality of range voltages VR1, VR2, VR3 and VR4. Each range voltage is a function of the reference voltage and represents one of a series of potential concentration ranges of the component in the test sample. VR likewise constitutes a range voltage, representing the lowest concentration range. For example, for the testing of chlorine, the range voltages VR1 through VR4 are selected so that each represents a whole number unit of chlorine in parts per million. Each range voltage is a logarithmic function of the reference voltage and is derived according to the formula outlined above. The voltages are generated from VR by employing resistors 110 that have a suitable resistance. In particular, VR, which represents the full reference voltage, corresponds to a concentration of 0 ppm. Voltage VR1 (0.562 VR) corresponds to a concentration of 1 ppm. Similarly, the remaining resistors in voltage divider 102 are selected so that VR2 (0.316 VR) represents a concentration of 2.0 ppm; VR3 (0.178 VR) represents a concentration of 3.0 ppm; and VR4 (0.1 VR) represents a concentration of 4.0 ppm. It has been determined that this is the practical upper range boundary for the photometric testing of chlorine in water.

Range computation means 120 are provided for comparing the respective range voltages with the test voltage VT and determining which concentration range applies to the sample being tested. More particularly, each of the voltages VR, VR1, VR2 and VR3 is applied as an input to a respective range comparator 122, 124, 126, and 128. The test voltage VT is applied as the other input to each comparator. If the applied test voltage VT is above the respective range voltage VR-VR3, the comparator 122 through 128 remains in a zero state and provides no output. If, however, the test voltage is equal to or below the respective range voltage input at the comparator, then that comparator provides a range output signal S over a respective line 130, 132, 134 or 136. For example, a test voltage of 0.4 VR, is above the level of VR2 (0.316 VR) and VR3 (0.7778 VR). However, it is below the voltage levels at VR and VR1. As a result, an output signal is provided by comparators 122 and 124 over lines 130 and 132, respectively. However, no signal is provided by comparators 126 and 128, respectively.

The signals S are provided to a range indicator logic 140. This logic typically comprises a plurality of gates that ascertain which of the comparators is providing a signal S. Logic 140 then activates an appropriate range indicator element LED 0, LED 1, LED 2 and LED 3 in group 24 so that the appropriate whole number concentration range (i.e. 0 ppm, 1 ppm, 2 ppm, 3 ppm, respectively) is displayed. For example, if logic 140 receives a signal from comparator 122 only, indicating that the concentration range is below 1 ppm, then only LED 0 is activated. If, as described above, signals are received from comparators 122 and 124, indicating that the concentration range is between 1 ppm and 2 ppm, then logic 140 activates only LED 1. If signals are received from comparators 122, 124 and 126, this indicates that the concentration level is between 2 ppm and 3 ppm. As a result, the logic activates only LED 2. Finally, if the logic receives signals S from each of the comparators, this indicates that the concentration is above 3 ppm and the logic activates LED 3. Various alternative comparator and logic schemes may also be employed.

The indicator circuit further includes means for determining and displaying incremental concentration levels of chlorine within each of the four concentration ranges 0-1 ppm, 1-2 ppm, 2-3 ppm, and 3-4 ppm. An incremental switch 150 selects the range voltages immediately above and below test voltage VT. If VT equals one of the range voltages then that voltage and the adjacent lower range voltage are selected. For example, if indicator logic 140 determine that only comparator 122 is on, then switch 150 selects voltage VR over line 152 and lower voltage VR1 over line 154. If the indicator logic reveals that all of the comparators 122-128 are providing an output signal S, then switch 150 selects VR3 and VR4 over lines 156 and 158, respectively. If, as described above the test voltage is 0.4 VR, then switch 150 selects VR1 over line 154 and VR2 over line 155.

The selected voltages are applied by switch 150 through buffer amplifiers 162 and 164, and across an incremental voltage divider 160. Voltage divider 160 comprises a resistor ladder including ten resistors 201 that divide the voltage drop VD across divider 160 into respective incremental voltage levels VD1, VD2 . . . VD9. Each incremental voltage level represents a certain percentage of the total voltage drop across the range and corresponds to an incremental concentration level of one tenth of a part per million (0.1 ppm) within that range. For chlorine, the following relationship applies:

| INCREMENTAL VOLTAGE, VDi | % OF VOLTAGE DIFFERENCE ACROSS RANGE | INCREMENTAL CONCENTRATION LEVEL |
|---|---|---|
| VD1 | .8727 VD | .1 ppm |
| VD2 | .7517 VD | .2 ppm |
| VD3 | .6354 VD | .3 ppm |
| VD4 | .53 VD | .4 ppm |
| VD5 | .4293 VD | .5 ppm |
| VD6 | .3326 VD | .6 ppm |
| VD7 | .2426 VD | .7 ppm |
| VD8 | .157 VD | .8 ppm |
| VD9 | .076 VD | .9 ppm |

It has been determined this above relationship applies to VD1-VD9 within each broad concentration range. Accordingly, the value of each resistor in voltage divider 160 is selected to provide the necessary fractional voltage drop which corresponds to a respective incremental level. In alternative embodiments, alternative voltage relationships may be utilized.

Incremental computation means 169 are provided for determining the appropriate incremental concentration of the component being tested. Each of the incremental voltages VD1-VD9 is applied as an input to a respective incremental voltage comparator 170-186. The test voltage derived from the test sample is applied as the other input to each of the incremental voltage comparators. Each comparator 170 through 186 alternates between two states. The comparator will be "off" if the test voltage is greater than a respective incremental voltage at that comparator. However, if the test voltage is equal to or less than its respective incremental voltage input, the comparator will be turned on and an output I will be provided over a respective line 190-206. The comparator signals I are provided to an incremental indicator logic 208, which activates an appropriate one of the LED's in group 26 to indicate the appropriate incremental concentration level. Incremental indicator logic 208 operates in a manner analogous to range indicator logic 140. Therefore, if only comparator 170 provides a signal I, then the logic 208 activates only LED 0.1. If, alternatively, comparators 170, 172, 174 and 176 provide output signals I, then the indicator logic activates only LED 0.4. The remaining LED's 0.2, 0.3, and 0.5 through 0.9 are individually activated by logic 208 in an analogous manner. In this way, the incremental level within the determined concentration range is measured and displayed. Only a single group of incremental LED's 26 are required for all four of the ranges.

In alternative embodiments, the incremental LED's 26 may be activated in various other patterns. For example, the number of LED's activated may correspond to the incremental concentration level.

Figure 3:
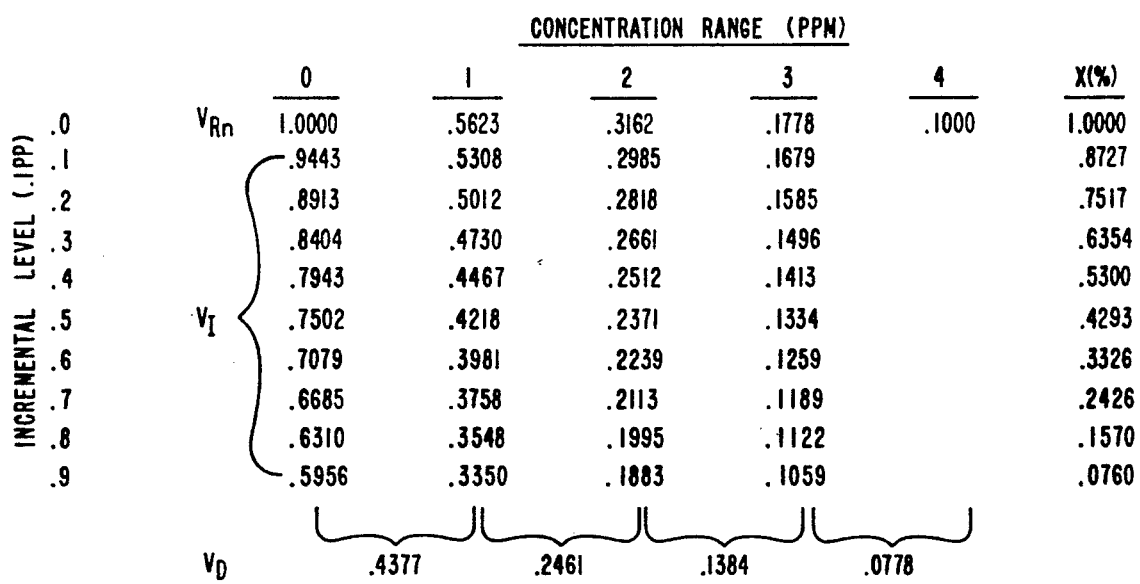
FIG. 3 is a table that represents various photometer voltage relationships according to this invention for incremental concentration levels of chlorine in water ranging from 0.0 ppm to 4.0 ppm.

FIG. 3 discloses a table of the relative voltages representing respective incremental concentration levels of chlorine in water. The whole unit numbers at the top of each column ("0", "1", "2", "3" and "4") represent the four continuous concentration ranges from 0 to 4 parts per million. The table lists the relative voltage, in terms of VR, at each increment of 0.1 ppm within each range. For example, at a concentration level of 0.0 ppm the relative voltage is 1 VR, which corresponds to the reference voltage. At a level of 0.1 ppm, the voltage level is 0.9443 VR, which indicates that a slight increase in concentration has correspondingly reduced the intensity of the light transmitted through the sample, and, as a result, the test voltage. At the opposite extreme of the table, higher levels of chlorine concentration significantly reduce the amount of light transmitted and, therefore, the test voltage. For example, at a concentration level of 3.8 ppm, the test voltage is 0.1122 VR, which represents only slightly more than one tenth the reference voltage level VR.

As indicated above, an important aspect of this invention is the realization that the relationship between a particular incremental voltage drop (e.g. representing an increase of 0.1 ppm, 0.2 ppm, etc.) within a broad concentration range and the voltage drop across the entire range is constant for each of the concentration ranges being tested. This relationship is expressed as follows:

$$X = \frac{VDi}{VD}$$

where VDi represents the incremental voltage drop and VD represents the voltage drop across the entire range. The voltage drop VD across each range 0-1 ppm, 1-2 ppm, 2-3 ppm and 3-4 ppm, is indicated by the row of numbers immediately below the table. The incremental voltage drop VDi represents the relative (in terms of VR) incremental voltage VI minus the range voltage immediately below that relative incremental voltage. Thus, $$VDi = Vi - VRn;$$

$$\text{therefore } X = \frac{VDi - VRn}{VD}$$

The constant X for each incremental level is referred to as the scale relative percentage. A column designated by the heading "X" appears at the right hand side of the table in FIG. 3. Each of the numbers in the column represents the constant percentage X at an associated incremental level within each of the four concentration ranges 0 through 3 ppm. For example, at an incremental level of 0.0 ppm, X is 1; at 0.1 ppm, X equals 0.8727, and so on.

The constant nature of X is illustrated by FIG. 3 and the following example:

At a incremental concentration level of 0.4 ppm, VI equals 0.7943 VR, VRn (the voltage level at 1 ppm,) is 0.5623 VR and VD (the voltage drop between 0 ppm and 1 ppm) is 0.4377 VR. Each of these values is entered into the formula $$X = \frac{VDi - VRn}{VD},$$

therefore $$X = \frac{.7943\ VR - .5623\ VR}{.4377\ VR} = .53$$

This result may be compared to the constant X at 1.4 ppm. At that level, VDi=0.4467, VRn=0.3162, and VD is 0.2461 VR. Accordingly, $$X = \frac{.4467\ VR - .3162\ VR}{.2461\ VR} = .53$$

A like ratio applies at concentration levels of 2.4 ppm and 3.4 ppm. The constant X may be determined and checked at each of the remaining incremental concentration levels in a similar manner.

After the constant X has been determined at each incremental level, the resistors of voltage divider 160 are selected to provide incremental voltage drops VD1-VD9 that correspond to X (VD). For example, the value the first resistor 201 is selected so that the incremental voltage drop at the first tap is 0.8727 VD; the second resistor provides a voltage at the second tap of 0.7517 VD; and so on.

The table and values illustrated in FIG. 3 are particularly appropriate for use in the measurement of chlorine in water. For alternative components and sample mediums, various other values are applicable. Nonetheless, the principle of employing a single voltage divider and an incremental computation circuit to determine the incremental concentration level, regardless of the broader concentration range, equally applies to such alternative embodiments.

The operation of photometer 10 is summarized as follows. Initially a water sample is added to cuvette 20 and placed in receptacle 18 without the addition of any reagent. Switch 32 is closed and lamp 14 is activated to provide a reference voltage VR. At the same time, zeroing circuit 42 is operated so that reference voltage VR is developed over line 92.

Cuvette 20 is then removed from receptacle 18 and a reagent is added and mixed well with the water. This turns the water a particular hue, which depends upon the concentration of chlorine in the water. Cuvette 20 is then returned to receptacle 18 and switch 34 is closed. This reactivates lamp 14, which transmits light through the cuvette such that detector 16 provides a test voltage VT, which is indicative of the intensity of the light, and therefore the concentration of chlorine in the test sample. Assume for purposes of illustration that VT=0.23 VR.

Reference voltage VR is applied across voltage divider 102, which divides VR into VR1-VR4. Each of these voltages is applied as one input to a respective comparator 122-128 and VT is applied as the other input. Because the test voltage, 0.23 is less than VR, VR1, and VR2, (i.e. 1 VR, 0.5623 VR and 0.3162 VR, respectively) comparators 122, 124 and 126 provide a signal S. However, VR3 is less than VT so no signal is provided by comparator 128. Signals S are received by indicator logic 140 which activates LED 2 in display 24 to indicate that the concentration level is at least 2 ppm.

Increment switch 150 selects VR2, which is 0.3162 VR, and VR3, which is 0.1778 VR and applies those voltages across voltage divider 160. This voltage drop is divided by the resistors in the voltage divider into respective incremental voltages VD1 through VD9, each of which is applied as one input to a respective comparator 170-186. Again, the test voltage VT is applied as the other input to each comparator. Referring to the table in FIG. 3, it can be seen that voltage level VD5, which represents a concentration level of 2.5 ppm is 0.2371. This voltage is greater than the test voltage VT. Accordingly, each of comparators 170-178 provides an incremental signal I to logic 208. The remaining incremental voltage levels VD6-VD9, i.e. 0.2239 through 0.1883 are less than VT so that comparators 180-186 remain "off". As a result, logic 208 activates only LED 0.5 of display 26. In this manner the appropriate concentration level of 2.5 ppm is displayed.

Although even smaller incremental levels of concentration may be determined by employing the circuitry of this invention, for most chlorine measurements an accuracy of tenths of parts per million is acceptable.

Although specific features of the invention are shown in some drawings and not in others, this is for convenience only, as each of the features may be combined with any or all of the other features in accordance with the invention.

Other embodiments will occur to those skilled in the art and are within the following claims:

What is claimed is:

1. An indicator circuit for an apparatus that measures the concentration of a selected component in a test sample, said circuit comprising:

means for generating a reference voltage that represents a known concentration of said component in a reference sample and a test voltage that represents the concentration of said component in said test sample;

a range voltage divider for dividing said reference voltage into a plurality of range voltages, each of which is a function of said reference voltage and represents one of a continuous series of potential concentration ranges of said component in said test sample;

range computation means for comparing said test voltage with each of said range voltages and determining the actual concentration range of said component in said test sample;

range indicator means, responsive to said range computation means, for indicating the determined concentration range of said component;

a incremental voltage divider;

switching means for selecting an adjacent pair of said range voltages, one of which is below and the other which is at least as great as said test voltage, and applying said selected range voltages across said incremental voltage divider such that the voltage difference of said selected range voltages is divided into a series of incremental voltages, each of which represents a respective one of a series of potential incremental concentration levels of said component within each said concentration range;

incremental computation means for comparing said test voltage with each of said incremental voltages and determining the actual incremental concentration level of said component in said test sample; and a group of incremental indicator elements, each of which represents a respective incremental concentration level within each said concentration range, said incremental indicator elements being responsive to said incremental computation means for indicating the determined incremental concentration level of said component in said test sample.

2. The circuit of claim 1 in which each said range voltage is a linear function of said reference voltage.

3. The circuit of claim 1 in which each said range voltage is a non-linear function of said reference voltage.

4. The circuit of claim 1 in which each said range voltage is a logarithmic function of said reference voltage.

5. An indicator circuit in an apparatus for measuring the concentration of a selected component in a test sample, which apparatus includes means for generating a test voltage that represents the concentration of the component in the test sample, said circuit comprising:
   means for generating a series of range voltages, each of which represents a respective one of a continuous series of potential concentration ranges of said component in said test sample;
   incremental voltage divider means;
   switching means for selecting an adjacent pair of said range voltages, one of which is below and the other of which is at least as great as said test voltage, and applying said selected range voltages across said incremental voltage divider means such that the voltage difference of said selected range voltages is divided into a series of incremental voltages, each of which represents a respective one of a series of potential incremental concentration levels of said component within each said concentration range;
   incremental computation means for comparing said test voltage with each of said incremental concentration voltages and determining the actual incremental concentration level of said component in said test sample; and
   a group of incremental indicator elements, each of which represents a respective incremental concentration level in each of said concentration ranges, said incremental indicator elements being responsive to said incremental computation means for indicating the determined incremental concentration level of said component in said test sample.

6. The circuit of claim 5 further including range computation means for comparing said test voltage with each of said range voltages and determining the actual concentration range of said component in said sample.

7. The circuit of claim 6 in which said range computation means include a group of range comparators, each of which compares said test voltage with a respective said range voltage and provides an output that represents the strength of said test voltage relative to that of said respective range voltage.

8. The circuit of claim 7 in which said range computation means include range logic means, responsive to said outputs from said range comparators, for directing said range indicator means to indicate the concentration range of said component in said test sample.

9. The circuit of claim 5 in which said range indicator means include a group of range indicator elements, each of which represents a respective concentration range.

10. The circuit of claim 5 in which said incremental computation means include a group of incremental level comparators, each of which compares said test voltage with a respective said incremental concentration voltage and provides an output representing the strength of said test voltage relative to said respective incremental concentration voltage.

11. The circuit of claim 10 in which said incremental computation means further include incremental logic means, responsive to said outputs of said incremental comparators for directing said incremental indicator elements to indicate the incremental concentration level of said components in said test sample.

12. A photometer for measuring the concentration of a selected component in a sample medium comprising:
   a selectively actuatable light source;
   means for alternately holding in the optical path of said light source a reference sample that represents a known concentration of said component in said medium and a test sample that represents the concentration to be measured;
   detector means for sensing the intensity of light transmitted through said reference sample and said test sample in a selected wavelength region and generating an output voltage representative of said sensed intensity;
   first means for actuating said light source to transmit light through said reference sample and means, responsive to said first means for actuating, for generating and storing a reference voltage that corresponds to said intensity sensed by said detector means when light is transmitted through said reference sample;
   second means for actuating said light source to transmit light through said test sample such that said output voltage comprises a test voltage;
   range voltage divider means for dividing said reference voltage into a plurality of range voltages, each of which is a function of said reference voltage and represents one of a continuous series of potential concentration ranges of said component in said test sample;
   range computation means for comparing said test voltage with each of said range voltages and determining the actual concentration range of said component in said test sample;
   range indicator means, responsive to said range computation means, for indicating the determined concentration range of said component;
   incremental voltage divider means;
   switching means for selecting an adjacent pair of said range voltages, one of which is below and the other of which is at least as great as said test voltage, and applying said selected range voltages across said second voltage divider such that the voltage difference of said selected range voltages is divided into a series of incremental voltages, each of which represents a respective one of a series of potential incremental concentration levels of said component within each said concentration range;
   incremental computation means for comparing said test voltage with each of said incremental concentration levels and determining the actual incremental concentration level of said constituent in said test sample; and
   a group of incremental indicator elements, each of which represents a respective incremental concentration level within each said concentration range, said incremental indicator elements being responsive to said incremental computation means for indicating the determined incremental concentration level of said component in said test sample.

13. The device of claim 12 in which said means for generating a reference voltage includes means for developing a staircase voltage that increases until it corresponds to said output voltage representing the intensity of light transmitted through said reference sample.

14. The device of claim 13 in which said means for developing include a pulse counter having an input and an output, a resistor ladder connected to said output of said counter, for driving said counter to provide a pulsed output signal to said resistor ladder, said ladder transforming said pulsed signal into said staircase voltage.

15. The device of claim 14 in which said means for driving include an oscillator.

16. The device of claim 13 in which said means for generating include means for comparing said staircase voltage and said output voltage and latching said means for developing in a condition that maintains said staircase voltage at a level that corresponds to said output voltage.

17. The device of claim 12 in which said second means for actuating include test timer means for holding said light source on for a predetermined time to transmit light through said test sample.

* * * * *